United States Patent [19]

Sharvit et al.

[11] Patent Number: 5,091,577
[45] Date of Patent: Feb. 25, 1992

[54] METHOD OF PREPARING FUNGICIDAL INTERMEDIATES

[75] Inventors: Joseph Sharvit, Lehavim; Abraham A. Pereferkovich, Kfar Sava, both of Israel

[73] Assignee: Makhteshim Chemical Works Ltd., Beer Sheva, Israel

[21] Appl. No.: 537,662

[22] Filed: Jun. 14, 1990

[30] Foreign Application Priority Data

Jun. 21, 1989 [IL] Israel .......................................... 90703

[51] Int. Cl.⁵ .................... C07C 213/02; C07C 217/30
[52] U.S. Cl. .................................... 564/399; 564/354; 564/353; 568/630; 568/655; 568/656
[58] Field of Search .................... 564/354, 399, 353; 514/651; 568/629, 630, 655, 656, 776, 774

[56] References Cited

U.S. PATENT DOCUMENTS 4,877,802 10/1989 Wilson et al. .................... 514/365

FOREIGN PATENT DOCUMENTS 0296373 12/1988 European Pat. Off. .
299892  1/1989 European Pat. Off. .

*Primary Examiner*—Glennon H. Hollrah
*Assistant Examiner*—Shailendra Kumar
*Attorney, Agent, or Firm*—Browdy and Neimark

[57] ABSTRACT

N-n-propyl-N-(2,4,6-trichlorophenoxy)-ethyl amine is prepared by reacting 2-phenoxy ethanol with thionyl chloride in the presence of a catalytic amount of tetraalkyl ammonium halide optionally in the presence of a solvent to form 2-phenoxy ethyl chloride; selectively chlorinating the 2-phenoxy ethyl chloride with chlorine at a temperature from 0° C. to 60° C. in the presence of a catalytic amount if urea to form 2-(2,4,6-trichlorophenoxy)-ethyl chloride; reacting the 2-(2,4,6-trichlorophenoxy)-ethyl chloride with n-propyl amine at a temperature of from 20° C. to 150° C., optionally in the presence of water; and recovering the N-n-propyl-N-2-(2,4,6-trichlorophenoxy)-ethyl amine formed.

18 Claims, No Drawings

5,091,577

1

METHOD OF PREPARING FUNGICIDAL INTERMEDIATES

BACKGROUND OF THE INVENTION

The present invention concerns the improved process for preparing 2-(2,4,6-trichlorophenoxy)-ethyl chloride and N-n-propyl-N-2-(2,4,6-trichlorophenoxy)-ethyl amine and their use in the manufacture of Prochloraz.

2-(2,4,6-Trichlorophenoxy)-ethyl chloride and N-n-propyl-N-2-(2,4,6-trichlorophenoxy)-ethyl amine are used as intermediates in the preparation of the fungicide Prochloraz.

According to GB 1,469,772, the classical method of preparing Prochloraz begins with 2,4,6-trichlorophenol. This process suffers from several disadvantages. First of all, the trichlorophenol must be in a highly pure form to avoid the formation of tarry by-products in the subsequent steps of preparing Prochloraz. Second, the processes used to purify 2,4,6-trichlorophenol most often lead to the formation of undesireable chlorinated by-products. Furthermore, the use of 2,4,6-trichlorophenol to prepare Prochloraz requires the reaction of the former under basic conditions, which can also lead to the formation of similar chlorinated by-products. Recent reports have tried to avoid the problems. Thus, EP 243,038 describes a process of preparing 2,4,6-trichlorophenol involving the slow controlled chlorination of phenol in the presence of a catalyst which is alleged to diminish the formation of the chlorinated by-products. EP 299,892 describes the chlorination of a chlorophenol using a different type of catalyst. Nevertheless, even if the formation of unwanted chlorinated by-products are avoided, the standard process for preparing Prochloraz according to GB 1,469,772 involves the need to handle 2,4,6-trichlorophenol and ethylene di-bromide-themselves both highly toxic and carcinogenic materials.

OBJECTIVES OF THE INVENTION

It is the objective of the present invention to provide a new and improved method for the preparation of 2-(2,4,6-trichlorophenoxy)ethyl chloride and N-n-propyl-N-2-(2,4,6-trichlorophenoxy)-ethyl amine. It is a further objective of the present invention to provide a method for the preparation of these compounds without having to handle the highly toxic and carcinogenic 2,4,6-trichlorophenol and ethylene dibromide. A further objective is the provision of a method for the prepara-tion of these compounds in high yields substantially free of the chlorinated by-products.

SUMMARY OF THE INVENTION

It has unexpectedly been discovered, that N-n-propyl-N-2-(2,4,6-trichlorophenoxy)-ethyl amine may be prepared comprising the steps of:

1. Reacting 2-phenoxy-ethanol with thionyl chloride in the presence of a catalytic amount of a tetra-alkyl ammonium halide at a temperature of from about 0° C. to 80° C., optionally in the presence of a solvent to form 2-phenoxy-ethyl chloride;

2. Selectively chlorinating the 2-phenoxy-ethyl chloride by reacting with chlorine at a temperature of from 0° C. to 60° C. in the presence of a catalytic amount of urea, to form 2-(2,4,6-trichlorophenoxy)-ethyl chloride.

3. Reacting the 2-(2,4,6-trichlorophenoxy)-ethyl chloride with n-propyl amine at a temperature of from 20° C. to 150° C., optionally in the presence of water, to

2 form N-n-propyl-N-2-(2,4,6-trichlorophenoxy)-ethyl amine.

4. Recovering the N-n-propyl-N-2-(2,4,6-trichlorophenoxy)-ethyl amine formed.

DETAILED DESCRIPTION OF THE INVENTION

The reaction process is generally illustrated below on a bath-wise basis:

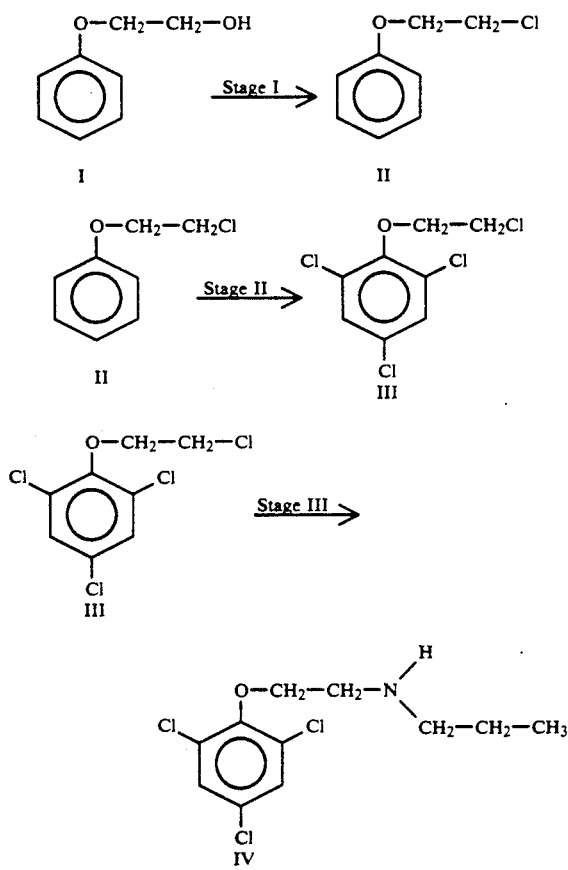

The temperature of reaction of Stage I may range from 0° C. to 80° C., but is preferably in the range of from 10° C. to 50° C.

In carrying out the process of Stage I of the present invention, equimolar amounts of thionyl chloride may be used. However, an excess of up to 20% is preferred to ensure complete reaction. This reaction may be carried out with or without a solvent. If a solvent is used, halogenated hydrocarbons such as chloroform, dichloromethane and carbon tetrachloride are preferred, with dichloromethane being most preferred.

The use of a catalyst such as a tetra-alkyl ammonium halide, was found necessary for this stage. The alkyl group of the tetra-alkyl ammonium halide may be chosen from the group consisting of straight or branched alkyl groups having from 1 to 16 carbon atoms, such as methyl, ethyl, propyl, butyl, pentyl, heptyl, decyl and the like, cyclic alkyl groups such as cyclopentyl, cyclohexyl, cycloheptyl, cyclodecyl and the like and benzyl. Preferred alkyl groups are straight chain alkyl groups having from 1 to 8 carbon atoms and benzyl. Most preferred are methyl and benzyl, with the preferred halide as chloride. An especially preferred catalyst is benzyl trimethyl ammonium chloride. The tetra-alkyl ammonium halide is used in a concentration of 0.5% to 10%, preferably 3%, based on the 2-phenoxy-ethanol.

In carrying out the process of Stage II of the present invention, chlorine is reacted with 2-phenoxy-ethyl chloride at a temperature of from 0° C. to 60° C., preferably from 5° C. to 40° C., in the presence of urea. The most suitable rate at which the chlorine gas is fed will vary with the reaction temperature. This stage can only be carried out by reacting at least three moles of chlorine per mole of 2-phenoxy-ethyl chloride. In practice, an excess of 20 percent of chlorine is used.

The reaction of Stage II can be carried out in a solvent chosen from the group consisting of carbon tetrachloride a mixture of water and carbon tetrachloride, and acetic acid, with acetic acid the most preferred solvent.

A small amount of urea was found to markedly improve the yield of the reaction and the purity of the product of Stage II. The ratio of urea to 2-phenoxy-ethyl chloride ranges from 1:4 to 1:50, preferably 1:4 to 1:20 and most preferably 1:10, by weight.

A reaction time of 6.5 hours in Stage II afforded a yield of 80% or better. When a shorter reaction time is used, such as 4.5 hours, the yield drops to less than 75%.

The temperature of reaction of Stage III may range from 20° C. to 150° C. At the lower end of the temperature range the reaction is too slow to be economical. At the higher end of the temperature range lower yields are obtained due to polymerization and decomposition. The preferred temperature range is from about 75° C. to 90° C.

Stage III may be either run neat or in the presence of water. It is preferred from a chemical point of view to run the reaction in water, for then a lower temperature (75° C. instead of 90° C.) and lower pressure (1.7 to 2.3 atmospheres instead of 2.2 to 3 atmospheres) can be used. However, for technical reasons, it is sometimes preferred to run this stage without water.

The final amine product can be isolated as a mineral acid salt, preferably as the hydrochloride acid addition salt, which forms nice white crystals which are easily handled. However, if necessary, the free amine may be isolated by treating the hydrochloride salt with a base such as, for example, aqueous sodium carbonate to neutralize to pH 7, separate the phases and distill the organic layer to yield an oil boiling at 112° C.–114° C. at 0.2 mm Hg.

Thus the present invention affords a process for preparing 2-(2,4,6-trichlorophenoxy)-ethyl chloride and N-n-propyl-N-2-(2,4,6-trichlorophenoxy)ethyl amine in high yield, without having to handle the highly toxic 2,4,6-trichlorophenol and ethylene dibromide. In addition, the latter amine product may be reacted with phosgene and subsequently with imidazole according to GB 1,469,772 to afford Prochloraz, having essentially no detectable amount of the undesireable chlorinated by-products.

While the invention will now be described in connection with certain preferred embodiments in the following examples, it will be understood that it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

EXAMPLE 1

Preparation of 2-phenoxyethyl chloride

Into a three-necked flask fitted with a stirrer, dropping funnel, thermometer and reflux condenser, was added 34.7 g 2-phenoxy-ethanol, 75 g dichloromethane and 1.25 g benzyl-trimethyl-ammonium chloride. The mixture was cooled to about 0° C. and 34 g thionyl chloride was added dropwise over a period of 45 minutes. After this addition, the mixture was warmed to room temperature, stirrer for an hour and then heated to reflux (50° C.) for an additional three hours. At the end of the reaction (determined by GLC) the mixture was washed with water, an aqueous 10% sodium hydroxide solution and then again with water. The solvent was distilled off to afford 40 g of 2-phenoxy-ethyl chloride in a concentration of 95%.

EXAMPLE 2

The same exact process of Example 1 was repeated without the use of solvent, where the only other difference was, that it was not necessary to remove any solvent after the washings. This afforded a similar yield of 2-phenoxy-ethyl chloride having the same purity.

EXAMPLE 3

Preparation of 2-(2,4,6-trichlorophenoxy)-ethyl chloride

Into a three-necked 250 ml flask fitted with a stirrer, thermometer and a gas bubbler, were added 20 g 2-phenoxy-ethyl chloride, 60 g acetic acid and 2 g urea. The mixture was cooled while stirring to 5° C. and the addition of chlorine gas was initiated. As the chlorination proceeded, the temperature of the reaction mixture was slowly raised, so that the third stage of chlorination took place at a temperature of 40° C. The overall reaction time was 6.5 hours. At the end of the reaction water was added, the organic phase separated and washed with water, then with sodium bisulfite solution, then with additional water. This afforded 28 g of 2-(2,4,6-trichlorophenoxy)-ethyl chloride in 80% yield. When exactly the same reaction was run with an overall reaction time of only 4.5 hours, a yield of only 74% was obtained.

EXAMPLE 4

Preparation of N-n-propyl-N-2-(2,4,6-trichlorophenoxy)-ethyl amine

Into a 1-liter glass reactor, which can withstand a pressure of 6 atmospheres, fitted with a stirrer, heating mantle and a pressure gauge, were added 270.8 g 2-(2,4,6-trichlorophenoxy)-ethyl chloride and 350 g n-propyl amine. The mixture was slowly heated with stirring over a period of 8 hours until a temperature of 90° C. was reached. The initial pressure under these conditions was 3 atmospheres, which drops during the reaction to about 2.2 atmospheres. The end of the reaction was determined by GLC. At the end of the reaction the mixture was cooled to 55° C., whereupon the pressure dropped to atmospheric. The excess n-propyl amine was distilled off and it could be recycled for use in a subsequent batch, until a bottom temperature of 85° C. was cooled to 40° C., 300 ml of a 20% hydrogen chloride solution and 1 g of an emulgator GAF RM-510 were added. The temperature rose to 70° C., the mixture was stirred for one hour at this temperature and the product precipitated as white crystals of the amine hydrochloride salt. The slurry was cooled to 40° C., filtered, reslurried in 250 ml xylene and filtered again. This afforded 297 g of white hydrochloride salt of N-n-propyl-N-2-(2,4,6-trichlorophenoxy)-ethyl amine in 93% yield and purity of 96%–98%.

EXAMPLE 5

Following the method of Example 4, the same reaction was run in the presence of 60 g water. The only differences were that the maximum temperature was only 75° C., with a total reaction time of only 5 hours; the initial pressure was 2.3 atmospheres and the final pressure 1.7 to 1.8 atmospheres. This afforded N-n-propyl-N-2-(2,4,6-trichlorophenoxy)-ethyl amine of similar yield and purity.

We claim:

1. A process for preparing N-n-propyl-N-2-(2,4,6-trichlorophenoxy)-ethyl amine of the formula:

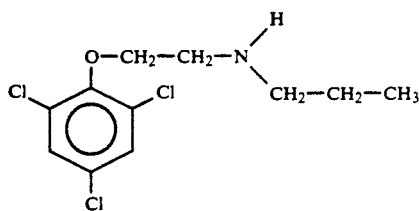

IV characterized in that:
a. 2-phenoxy ethanol of the formula

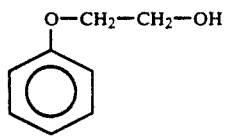

I is reacted with thionyl chloride in the presence of a catalytic amount of a tetra-alkyl ammonium halide having from 1–16 carbon atoms or benzyl trimethyl ammonium halide at a temperature of from about 0° C. to 50° C. optionally in the presence of a solvent, to form 2-phenoxy-ethyl chloride of the formula:

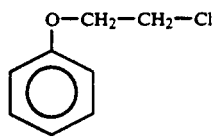

II b. the 2-phenoxy-ethyl chloride is selectively chlorinated by reacting it with chlorine at a temperature of from 0° C. to 60° C. in the presence of a catalytic amount of urea to form 2-(2,4,6-trichlorophenoxy)-ethyl chloride of the formula:

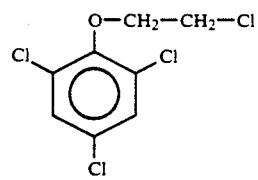

III c. the 2-(2,4,6-trichlorophenoxy)-ethyl chloride is reacted with n-propyl amine at a temperature of from 20° C. to 150° C., optionally in the presence of water, to form N-n-propyl-N-2-(2,4,6-trichlorophenoxy)-ethyl amine; and d. the N-n-propyl-N-2-(2,4,6-trichlorophenoxy)-ethyl amine formed is recovered.

2. A process in accordance with claim 1 wherein the solvent of Stage I is a chlorinated hydrocarbon.

3. A process in accordance with claim 1 wherein the solvent of Stage I is chosen from the group consisting of chloroform, dichloromethane and carbon tetrachloride.

4. A process in accordance with claim 1 wherein the solvent of Stage I is dichloromethane.

5. A process in accordance with claim 1 wherein the tetra-alkyl ammonium halide in Stage I is tetra-alkyl ammonium chloride.

6. A process in accordance with claim 1 wherein the alkyl groups of the tetra-alkyl ammonium halide in Stage I are chosen from the group consisting of straight chain alkyl groups having from 1 to 6 carbon atoms.

7. A process in accordance with claim 1 wherein the ammonium halide in Stage I is benzyl-trimethyl-ammonium chloride.

8. A process in accordance with claim 1 wherein the tetra-alkyl ammonium halide in Stage I is present at a concentration of from 0.5% to 10%, based on the 2-phenoxy-ethanol.

9. A process in accordance with claim 1 wherein the temperature of Stage I ranges from about 10° C. to 50° C.

10. A process in accordance with claim 1 wherein the temperature of Stage II ranges from about 5° C. to 40° C.

11. A process in accordance with claim 1 wherein the molar ratio of urea to 2-phenoxy-ethyl chloride in Stage II ranges from 1:4 to 1:50 by weight.

12. A process in accordance with claim 1 wherein the molar ratio of urea to 2-phenoxy-ethanol in Stage II is 1:10 by weight.

13. A process in accordance with claim 1 wherein Stage II is run in a solvent chosen from the group consisting of carbon tetrachloride, a mixture of water and carbon tetrachloride, and acetic acid.

14. A process in accordance with claim 1 wherein Stage II is run in acetic acid as solvent.

15. A process in accordance with claim 1 wherein Stage III is run in the presence of water.

16. A process in accordance with claim 1 wherein the temperature of Stage III ranges from about 75° C. to 90° C.

17. A process for preparing N-n-propyl-N-2-(2,4,6-trichlorophenoxy)-ethyl amine characterized in that:
a. reacting 2-Phenoxy-ethanol with thionyl chloride in the presence of benzyl-trimethylammonium chloride in a molar ratio of 28:1 respectively, in dichloromethane as solvent, at a temperature of from about 0° C. to 50° C. to form 2-phenoxy-ethyl chloride;

b. reacting the 2-phenoxy-ethyl chloride with chlorine in acetic acid as solvent, at a temp. of from 5° C. to 40° C. in the presence of urea in a weight ratio of urea to 2-phenoxy-ethyl chloride of 1:10 to form 2-(2,4,6-trichlorophenoxy)-ethyl chloride;

c. reacting the 2-(2,4,6-trichlorophenoxy)-ethyl chloride with n-propyl-amine in the presence of water at a temperature of from 75° C. to 90° C. to form N-n-propyl-N-2-(2,4,6-trichlorophenoxy)-ethyl amine; and d. recovering the N-n-propyl-N-2-(2,4,6-trichlorophenoxy)-ethyl amine formed.

18. A process for preparing 2-(2,4,6-trichlorophenoxy)-ethyl chloride characterized in that:

a. reacting 2-phenoxyethanol with thionyl chloride in the presence of benzyl-trimethyl-ammonium chloride in a molar ratio of 28:1 respectively in dichloromethane as solvent, at a temperature of from about 0° C. to 50° C. to form 2-phenoxyethyl chloride;

b. reacting the 2-phenoxy-ethyl chloride with chlorine in acetic acid as solvent, at a temp. of from 5° C. to 40° C. in the presence of urea in a weight ratio of urea to 2-phenoxy-ethyl chloride of 1:10 to form 2-(2,4,6-trichlorophenoxy)-ethyl chloride; and c. recovering the 2-(2,4,6-trichlorophenoxy)-ethyl chloride formed.

* * * * *